US00PP26688P2

(12) United States Plant Patent
Graff

(10) Patent No.: US PP26,688 P2
(45) Date of Patent: May 3, 2016

(54) ***HIBISCUS* PLANT NAMED 'MULTI TROPIC ORANGE'**

(50) Latin Name: *Hibiscus rosa-sinensis*
Varietal Denomination: Multi Tropic Orange

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 112 days.

(21) Appl. No.: 14/120,535

(22) Filed: May 31, 2014

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Annette Para
(74) *Attorney, Agent, or Firm* — C. A. Whealy

(57) ABSTRACT

A new and distinct cultivar of *Hibiscus* plant named 'Multi Tropic Orange', characterized by its upright, uniformly mounding and bushy plant habit; shiny dark green-colored leaves; uniform, continuous and freely flowering habit; bright orange-colored flowers with dark red-colored centers; and good flower longevity.

2 Drawing Sheets

Botanical designation: *Hibiscus rosa-sinensis*.
Cultivar denomination: 'MULTI TROPIC ORANGE'.

BACKGROUND OF THE INVENTION

The present invention relates to a new and distinct cultivar of *Hibiscus* plant, botanically known as *Hibiscus rosa-sinensis*, and hereinafter referred to by the name 'Multi Tropic Orange'.

The new *Hibiscus* plant is a product of a planned breeding program conducted by the Inventor in Sabro, Denmark. The objective of the breeding program is to create new compact, uniform, strong and freely-branching *Hibiscus* plants with continuous flowering and attractive long-lasting flowers.

The new *Hibiscus* plant originated from a cross-pollination conducted by the Inventor in April, 2007 in Sabro, Denmark of *Hibiscus rosa-sinensis* 'Calypso Wind', disclosed in U.S. Plant Pat. No. 10,947, as the female, or seed, parent with *Hibiscus rosa-sinensis* 'Caroline', disclosed in U.S. Plant Pat. No. 11,779, as the male, or pollen, parent. The new *Hibiscus* plant was discovered and selected by the Inventor as a flowering plant within the progeny of the stated cross-pollination in a controlled greenhouse environment in Sabro, Denmark in July, 2008.

Asexual reproduction of the new *Hibiscus* plant by vegetative terminal cuttings in a controlled greenhouse environment in Sabro, Denmark since October, 2008 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Multi Tropic Orange'. These characteristics in combination distinguish 'Multi Tropic Orange' as a new and distinct *Hibiscus* plant:

1. Upright, uniformly mounding and bushy plant habit.
2. Shiny dark green-colored leaves.
3. Uniform, continuous and freely flowering habit.
4. Bright orange-colored flowers with dark red-colored centers.
5. Good flower longevity.

Plants of the new *Hibiscus* can be compared to plants of the female parent, 'Calypso Wind'. Plants of the new *Hibiscus* differ primarily from plants of 'Calypso Wind' in the following characteristics:

1. Plants of the new *Hibiscus* have smaller flowers than plants of 'Calypso Wind'.
2. Plants of the new *Hibiscus* and 'Calypso Wind' differ in flower color as plants of 'Calypso Wind' have lighter orange-colored flowers.
3. Flowers of plants of the new *Hibiscus* are not as long-lasting as flowers of plants of 'Calypso Wind'.

Plants of the new *Hibiscus* can be compared to plants of the male parent, 'Caroline'. Plants of the new *Hibiscus* differ primarily from plants of 'Caroline' in the following characteristics:

1. Plants of the new *Hibiscus* and 'Caroline' differ in leaf shape.
2. Plants of the new *Hibiscus* and 'Caroline' differ in flower color as plants of 'Caroline' have lighter orange-colored flowers.
3. Flowers of plants of the new *Hibiscus* are longer-lasting than flowers of 'Caroline'.

Plants of the new *Hibiscus* can be compared to plants of the *Hibiscus rosa-sinensis* 'Laluna', disclosed in U.S. Plant Pat. No. 24,061. In side-by-side comparisons conducted in Sabro, Denmark, plants of the new *Hibiscus* differed from plants of 'Laluna' in the following characteristics:

1. Plants of the new *Hibiscus* and 'Laluna' differed slightly in leaf shape.

2. Plants of the new *Hibiscus* and 'Laluna' differed in flower form as plants of 'Laluna' had double-type flowers.
3. Plants of the new *Hibiscus* and 'Laluna' differed in flower color as plants of 'Laluna' had lighter orange-colored flowers.
4. Flowers of plants of the new *Hibiscus* were not as long-lasting as flowers of plants of 'Laluna'.

Plants of the new *Hibiscus* can be compared to plants of the *Hibiscus rosa-sinensis* 'Apollo', disclosed in U.S. Plant Pat. No. 23,072. In side-by-side comparisons conducted in Sabro, Denmark, plants of the new *Hibiscus* differed from plants of 'Apollo' in the following characteristics:

1. Plants of the new *Hibiscus* and 'Apollo' differed in leaf shape.
2. Plants of the new *Hibiscus* had smaller flowers than plants of 'Apollo'.
3. Plants of the new *Hibiscus* and 'Apollo' differed in flower color.
4. Flowers of plants of the new *Hibiscus* were not as long-lasting as flowers of plants of 'Apollo'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Multi Tropic Orange' grown in a container.

The photograph on the second sheet is a close-up view of typical developing flower buds and a typical open flower of 'Multi Tropic Orange'.

DETAILED BOTANICAL DESCRIPTION

The aforementioned photographs and following observations, measurements and values describe plants grown during the autumn and winter in 13-cm containers in a glass-covered greenhouse in Sabro, Denmark and under cultural practices typical of commercial *Hibiscus* production. During the production of the plants, day temperatures ranged from 20° C. to 25° C., night temperatures ranged from 19° C. to 21° C. and light levels ranged from 40 to 50 klux. Plants were pinched one time about nine to ten weeks after planting. Plants were 24 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Multi Tropic Orange'.

Parentage:

*Female, or seed, parent.*—*Hibiscus rosa-sinensis* 'Calypso Wind', disclosed in U.S. Plant Pat. No. 10,947.

*Male or pollen parent.*—*Hibiscus rosa-sinensis* 'Caroline', disclosed in U.S. Plant Pat. No. 11,779.

Propagation:

*Type.*—By vegetative terminal cuttings.

*Time to initiate roots, summer and winter.*—About four weeks at temperatures about 24° C.

*Time to produce a rooted young plant, summer.*—About nine weeks at temperatures about 24° C.

*Time to produce a rooted young plant, winter.*—About ten weeks at temperatures about 24° C.

*Root description.*—Medium in thickness, fleshy; color, close to 158A.

*Rooting habit.*—Freely branching; dense.

Plant description:

*Plant and growth habit.*—Upright, uniformly mounding and bushy plant habit; moderately vigorous growth habit.

*Branching habit.*—Freely branching habit with usually about four to six lateral branches developing per plant; pinching enhances lateral branch development.

*Plant height.*—About 35 cm to 55 cm.

*Plant diameter* (*area of spread*).—About 30 cm to 50 cm.

Lateral branch description:

*Length.*—About 15 cm to 25 cm.

*Diameter.*—About 4 mm to 8 mm.

*Internode length.*—About 1 cm to 5 cm.

*Strength.*—Strong.

*Texture.*—Smooth, glabrous; with development, becoming woody.

*Color, developing.*—Close to 146A.

*Color, developed.*—Close to 197A.

Leaf description:

*Arrangement.*—Alternate, single; numerous.

*Length.*—About 8 cm to 10 cm.

*Width.*—About 6 cm to 7 cm.

*Shape.*—Ovate to cordate.

*Apex.*—Acuminate.

*Base.*—Obtuse to cordate.

*Margin.*—Crenate to dentate.

*Texture, upper surface.*—Smooth, glabrous; venation, recessed.

*Texture, lower surface.*—Scattered pubescence; venation, prominent.

*Luster, upper surface.*—Glossy.

*Luster, lower surface.*—Slightly glossy.

*Venation pattern.*—Pinnate; arcuate.

*Color.*—Developing leaves, upper surface: Close to 137A. Developing leaves, lower surface: Close to 146A. Fully expanded leaves, upper surface: Close to N189A; venation, close to 146A. Fully expanded leaves, lower surface: Close to 147A; venation, close to 146C.

*Petioles.*—Length: About 4 cm to 6 cm. Diameter: About 1.5 mm to 2 mm. Texture, upper and lower surfaces: Pubescent. Color, upper surface: Close to 147A. Color, lower surface: Close to 146A.

Flower description:

*Flower arrangement.*—Flowers arranged singly at terminal leaf axils; uniform, continuous and freely flowering habit with numerous flower buds and open flowers per plant at one time; flowers face mostly upright to slightly outwardly.

*Fragrance.*—None detected.

*Natural flowering season.*—Plants flower in the garden during the spring and summer or during periods of warm weather; in the greenhouse, plants can be flowered year-round; plants begin flowering about 10 to 14 weeks after pinching.

*Flower longevity.*—Good flower longevity, flowers last about two days on the plant; flowers persistent.

*Flower diameter*.—About 12 cm to 15 cm.

*Flower length* (*height*).—About 8 cm to 9 cm.

*Flower buds*.—Length: About 4 cm to 6 cm. Diameter: About 1.5 cm to 2 cm. Shape: Ovate to lanceolate. Color: Close to 34A and 150B.

*Petals*.—Arrangement: Five imbricate petals in a single whorl. Length: About 8 cm. Width: About 6 cm. Shape: Fan-shaped. Apex: Rounded. Base: Attenuate. Margin: Entire, slightly undulate. Texture, upper and lower surfaces: Glabrous, rugose; venation, slightly prominent. Luster, upper and lower surfaces: Matte. Color: When opening, upper surface: Close to 34A; towards the base, close to 46A. When opening, lower surface: Close to 34A and 150B. Fully opened, upper surface: Close to N30B; towards the base, close to 46A; venation, close to 31A; with development, main color becoming closer to 33A. Fully opened, lower surface: Close to 33B and 1C; venation, close to 1C; with development, main color becoming closer to N34B.

*Sepals*.—Appearance: Five sepals fused into a campanulate-shaped calyx. Length: About 3 cm. Width: About 1.2 cm to 1.5 cm. Shape: Lanceolate. Apex: Acuminate. Margin: Entire. Texture, upper surface: Rugose, pubescent; venation, prominent. Texture, lower surface: Slightly pubescent; venation, recessed. Luster, upper surface: Matte. Luster, lower surface: Glossy. Color, upper surface: Close to 144A. Color, lower surface: Close to 143C.

*Peduncles*.—Length: About 3 cm to 4 cm. Diameter: About 2 mm to 3 mm. Strength: Strong. Texture: Sparsely pubescent. Color, upper surface: Close to 146A. Color, lower surface: Close to N199B.

*Reproductive organs*.—Androecium: Stamen number: Numerous, about 100. Staminal column length: About 6 cm to 7 cm. Staminal column color: Towards the base, close to 34A; mid-section, close to 30A; and towards the apex, close to 32B. Filament length: About 3 mm. Filament color: Close to 32A. Anther shape: Ovate, rounded. Anther length: About 1 mm to 2 mm. Anther color: Close to 19A. Amount of pollen: Abundant. Pollen color: Close to 17A. Gynoecium: Pistil length (including staminal column): About 7 cm to 8 cm. Style texture: Smooth, waxy. Style color: Close to 11D. Stigma appearance: Five-parted, rounded. Stigma color: Close to 46B. Ovary color: Close to 145C.

*Seeds and fruits*.—Seed and fruit development have not been observed on plants of the new *Hibiscus*.

Temperature tolerance: Plants of the new *Hibiscus* have been observed to have tolerate temperatures from about 1° C. to about 30° C.

Pathogen & pest resistance: Plants of the new *Hibiscus* have not been observed to be resistant to pathogens and pests common to *Hibiscus* plants.

It is claimed:

1. A new and distinct *Hibiscus* plant named 'Multi Tropic Orange' as illustrated and described.

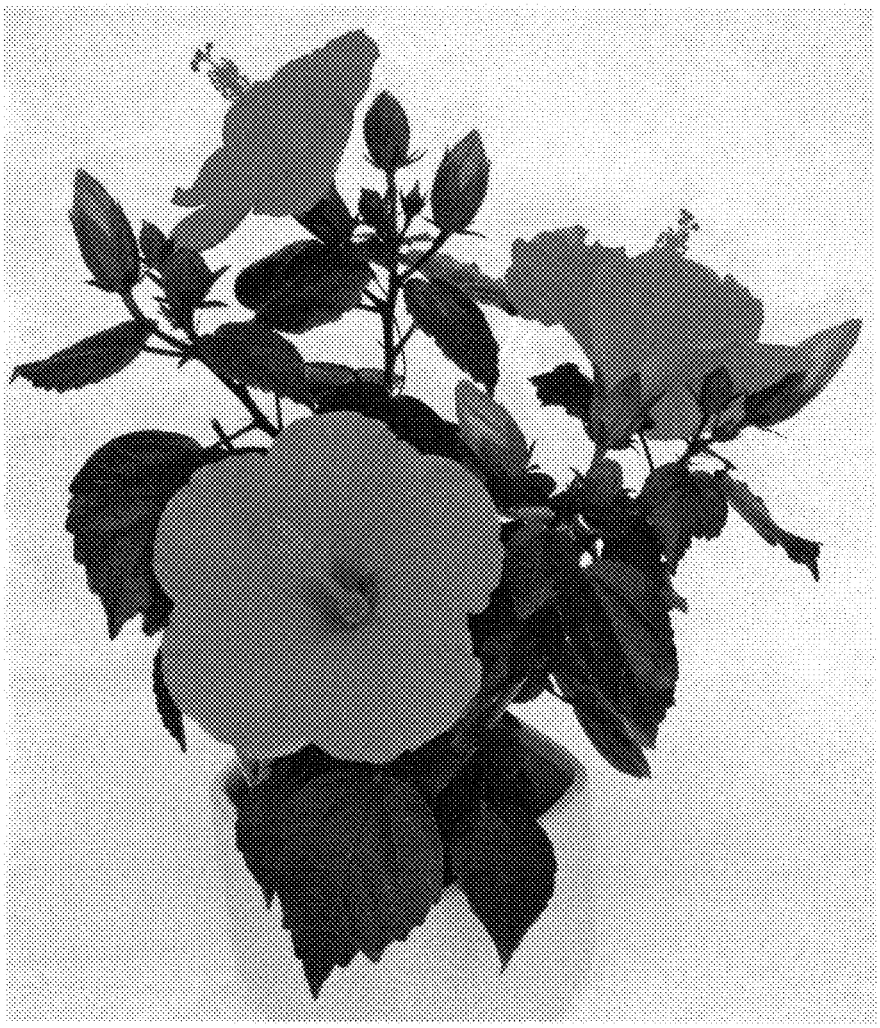

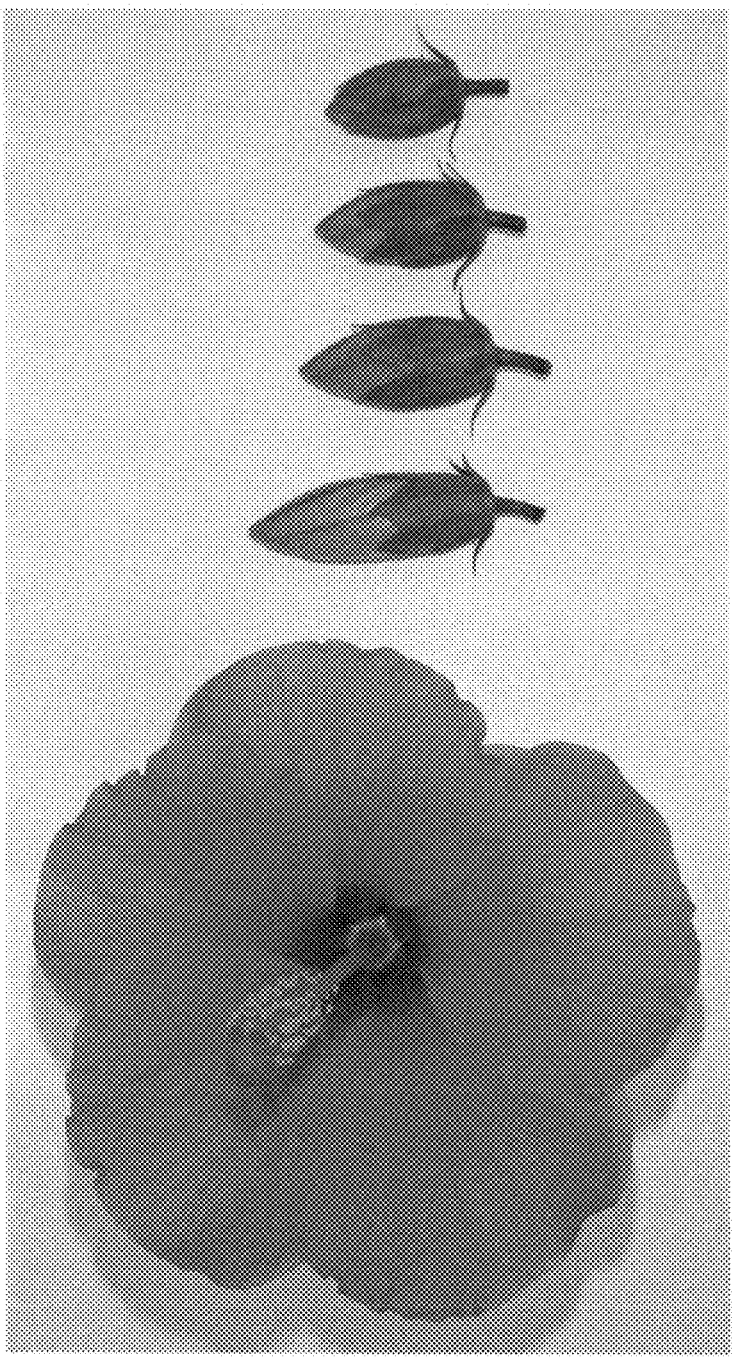

* * * * *